United States Patent

Curran

[11] 4,000,278
[45] Dec. 28, 1976

[54] QUINOLINE DERIVATIVES
[75] Inventor: Adrian Charles Ward Curran, Newcastle-upon-Tyne, England
[73] Assignee: John Wyeth & Brother Limited, Maidenhead, England
[22] Filed: Apr. 8, 1975
[21] Appl. No.: 566,639
[30] Foreign Application Priority Data
Apr. 19, 1974 United Kingdom ............ 17224/74
Dec. 3, 1974 United Kingdom ............ 52242/74
[52] U.S. Cl. .................... 424/257; 260/279 R; 260/287 CF; 260/283 R; 260/283 CN; 260/283 SY; 424/258
[51] Int. Cl.[2] ............... C07D 219/04; A61K 31/47
[58] Field of Search ..... 260/279 R, 283 S, 287 CF, 260/288 CF; 424/257, 258
[56] References Cited
UNITED STATES PATENTS
3,232,945  2/1966  Sigal, Jr. et al. ............ 260/288 CF
FOREIGN PATENTS OR APPLICATIONS
2,352,585  5/1974  Germany
OTHER PUBLICATIONS
Patnaik et al., J. Med. Chem., vol. 9, pp. 483-488, (1966).
Borsche et al., Chemical Abstracts, v. 32, 4587[4] (1938).
Kempter et al., Chemical Abstracts, v. 60, 6822h (1964).

Primary Examiner—Donald G. Daus
Assistant Examiner—Diana G. Rivers

[57] ABSTRACT

This application concerns quinoline derivatives of formula I

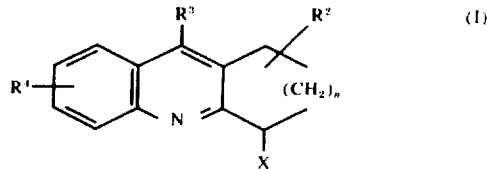

and pharmaceutically acceptable acid addition salts thereof, wherein X represents $CSNHR^1$, where $R^1$ represents hydrogen or lower alkyl, $R^2$ and $R^3$ are the same or different and represent hydrogen or lower alkyl, $R^4$ represents hydrogen or single or multiple substitution by lower alkyl and $n$ is 1, 2 or 3.

These compounds are anti-ulcer agents.

8 Claims, No Drawings

QUINOLINE DERIVATIVES

The invention relates to quinoline derivatives to processes for preparing them and to pharmaceutical compositions containing them.

The invention provides compounds of formula I

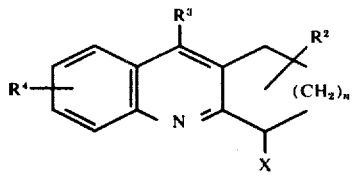
(I)

and pharmaceutically acceptable acid addition salts thereof, wherein X represents $CSNHR^1$, where $R^1$ represents hydrogen or lower alkyl, $R^2$ and $R^3$ are the same or different and represent hydrogen or lower alkyl, $R^4$ represents hydrogen or single or multiple substitution by lower alkyl and n is 1, 2 or 3.

When any of $R^1$, $R^2$, $R^3$ and $R^4$ represents a lower alkyl radical this may be a straight or branched chain, having from 1 to 6 carbon atoms, e.g. methyl, ethyl, n-, iso-propyl and n-, s- and t-butyl. The term alkyl radical is also intended to embrace cyclic alkyl radicals e.g. cyclobutyl, cyclopentyl and cyclohexyl.

Particularly preferred compounds are those in which $R^2$, $R^3$, and $R^4$ are hydrogen and $R^1$ is hydrogen or methyl. Also preferred are compounds wherein n is 1 or 2.

In a preferred aspect the present invention provides compounds of formula (III).

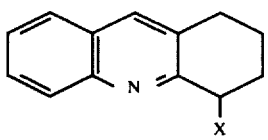
(III)

and pharmaceutically acceptable acid addition salts thereof, wherein X is as defined in connection with formula I.

Preferably X is $CSNH_2$ or CSNHMe.

Preferred compounds of the invention are 1,2,3,4-tetrahydroacridine-4-thiocarboxamide, 1,2,3,4-tetrahydroacridine-4-(N-methyl)-thiocarboxamide and their pharmaceutically acceptable acid addition salts.

The compounds of formula I can form acid addition salts with inorganic acids e.g. hydrochloric, hydrobromic, sulphuric or nitric acids or organic acids e.g. citric, fumaric, maleic or tartaric acids. These acid addition salts are included in the invention.

In the compounds of formula I the carbon atom to which X is attached is asymmetric. Consequently the compounds can exist in optically active d and l forms. These optically active forms and the racemates are included in the invention. The optically active forms may be separated by standard techniques either by formation of an acid salt with an optically active acid or by use of an optically active base with a compound in which X is COOH and conversion of the separated isomers to corresponding compounds where X is $CSNHR^1$.

Compounds of formula I, wherein X is $CSNHR^1$ are anti-ulcer agents which display activity in the anti-ulcer test method of Brodie and Hanson, J. Applied Physiology, 15, 291, 1960 or the anti-secretory test of H. Shay, D. Sun and H. Greenstein, Gastroenterology 1954, 26, 906–13.

The compounds of formula I may be prepared by various methods all of which are included in the invention.

A general method of preparing the compounds of formula I comprises treating a corresponding compound in which X is hydrogen to introduce the desired group X, e.g. by known methods.

A preferred method for preparing compounds of formula I wherein X is $CSNH_2$ comprises treating a compound of formula IV

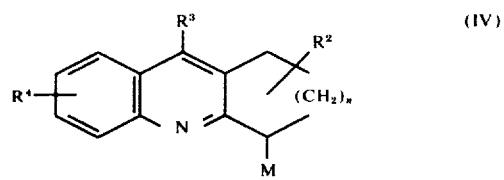
(IV)

wherein $R^2$, $R^3$, $R^4$ and n are as defined in connection with formula I and M is sodium, potassium, lithium or MgHal where Hal is chlorine, bromine or iodine, with a compound of formula $R_xSi(NCS)_{4-x}$ wherein R is an alkyl, aryl or aralkyl residue and Rx may be any mixture of these, and x is 0, 1, 2 or 3, and subjecting the product to hydrolysis or alcoholysis.

Compounds of formula IV wherein M is sodium, potassium or lithium may be prepared by reacting a compound of formula I wherein X is hydrogen with a metal alkyl $MR^5$ wherein $R^5$ is alkyl, aryl or aralkyl. The alkyl radical $R^5$ may have any of the values discussed above for the similar radicals $R^2$ and $R^3$. Examples of aryl radicals are phenyl which may be substituted by alkyl, halogen, nitro or trifluoromethyl. Examples of aralkyl radicals are phenyl lower alkyl radicals wherein the lower alkyl portion may have any of the values discussed above for the lower alkyl radicals $R^1$, $R^2$, $R^3$ and $R^4$. $R^5$ is preferably n-butyl or phenyl. Preferred compounds $MR^5$ are n-butyl lithium and phenyl lithium.

Compounds of formula IV wherein M is MgHal may be prepared by treating a compound of formula I wherein X is hydrogen, with an alkyl magnesium halide, $R^6MgHal$ wherein $R^6$ is an alkyl group, preferably a lower alkyl group and Hal is chlorine, bromine or iodine. $R^6$ may be a straight or branched chain alkyl group, the isopropyl group being preferred.

The reaction is conducted in an inert atmosphere, preferably in the presence of an inert solvent with a boiling point in the range 100°–120° C e.g. toluene or dioxan, toluene being the preferred solvent. The reaction may be carried out in the absence of a solvent but the yields are generally lower unless an excess of the Grignard reagent is used.

Conveniently the compound of formula (IV) is prepared in situ and then treated with the compound of formula $R_xSi(NCS)_{4-x}$ followed by hydrolysis or alcoholysis to obtain the desired compound of formula 1.

Examples of the compound $R_xSi(NCS)_{4-x}$ are $Si(NCS)_4$, $RSi(NCS)_3$, $R_2Si(NCS)_2$ and $R_3SiNCS$. Preferably the radical $R_x$ is trialkyl, triaryl or triaralkyl, triloweralkyl, e.g. trimethyl, being preferred.

The reaction with the compound $R_xSi(NCS)_{4-x}$ is conducted under anhydrous conditions, preferably in an inert solvent for example a hydrocarbon solvent such as benzene, toluene, or hexane. Ethers including cyclic ethers such as tetrahydrofuran should be avoided. Conveniently the starting material of formula II is prepared in situ and the same solvent is used for the reaction with the compound of formula $R_xSi(NCS)_{4-x}$.

Substituted thioamides of formula I wherein X is $CSNHR^1$ and $R^1$ is lower alkyl may be prepared by treatment of a thioamide of formula I, wherein X is $CSNH_2$ with an amine of formula $R^1NH_2$ wherein $R^1$ is lower alkyl in the presence of $H_2S$. Further methods of preparing thioamides will be discussed below.

Compounds of formula I in which X is $CO_2R^1$ are intermediates for preparing the thioamides of formula I. These intermediates may be prepared by treating a compound of formula IV with carbon dioxide to produce a compound of formula I wherein X is $CO_2M$ where M is as defined in connection with formula IV and then with an alcohol $R^1OH$ wherein $R^1$ is a lower alkyl group in the presence of an acid catalyst, e.g. dry HCl gas or conc. sulphuric acid. Compounds of formula I wherein X is $CO_2H$ may be obtained by treatment of a compound of formula (IV) with acid e.g. hydrobromic or hydrochloric acid.

The esterification of a compound of formula I in which X is $CO_2H$ may be carried out using an hydroxyl compound $R^1OH$, wherein $R^1$ is alkyl according to standard procedures, e.g. in the presence of an acid catalyst e.g some concentrated sulphuric acid or after saturation with hydrogen chloride gas or a Lewis acid e.g. boron trifluoride if desired with heat or treatment of the silver salt, (X is COOAg) with an iodide $R^1I$ wherein $R^1$ is alkyl.

The yield of ester may be improved by treating a compound of formula I wherein X is hydrogen with a metal alkyl $MR^5$ followed by $CO_2$ then a further quantity of the metal alkyl after the $CO_2$ treatment, followed by a further amount of $CO_2$. It is believed that the further quantity of metal alkyl and $CO_2$ gives the bis acid metal salt of formula V

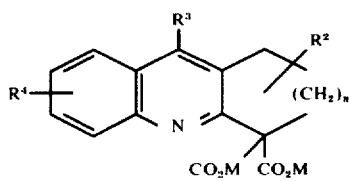

wherein $R^2$, $R^3$ and $R^4$ are as defined in connection with formula I and M is sodium, potassium or lithium, and this salt spontaneously decarboxylates during the esterification.

A further method for preparing esters of formula I wherein X is $CO_2R^1$ comprises treating a compound of formula I as defined above wherein X is a hydrogen atom with a metal alkyl $MR^5$ and then treating the product with a haloformate of formula $HalCOOR^1$ wherein Hal is a halogen atom e.g. chlorine or bromine and $R^1$ is alkyl. The product is usually a mixture of the desired compound of formula I wherein X is $CO_2R^1$ wherein $R^1$ is alkyl and the corresponding bis-ester of formula (VI)

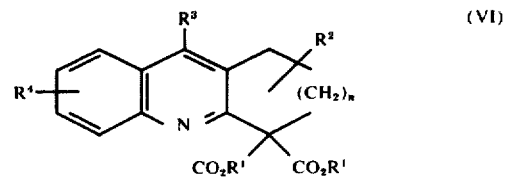

wherein $R^1$ is alkyl and $R^2$, $R^3$, $R^4$ and $n$ are as defined in connection with formula I. These bis-esters are useful for preparing the corresponding compounds of formula I wherein X is $CO_2H$. This mixture of mono and bis-esters may be converted directly to the corresponding compound of formula I where X is $CO_2H$, by saponification with an alkaline earth metal hydroxide to give a mixture of the metal salt of the mono acid of formula I wherein X is $CO_2H$ and the metal salt of the diacid of formula (VI) wherein $R^1$ is H. Treatment of this mixture with a mineral acid e.g. hydrochloric acid gives the desired acid of formula I wherein X is $CO_2H$ since the diacid spontaneously decarboxylates to form the mono acid.

The product of the haloformate reaction may be treated with a further quantity of the metal alkyl followed by a further quantity of the haloformate thereby producing more of the bis ester (VI).

A further method for preparing compounds of formula I in which X is $CO_2H$ comprises decarboxylation of a compound of formula (VI). The decarboxylation may be carried out by heating the dicarboxylic acid of formula VI wherein $R^1$ is hydrogen. Usually the dicarboxylic acid is prepared in situ by hydrolysis of the corresponding di-ester, wherein $R^1$ is alkyl. The hydrolysis and decarboxylation may be carried out by heating with a dilute mineral acid e.g. HCl or sulphuric acid or the diester may be saponified with alkali e.g. sodium or potassium hydroxide. The resulting salt is then acidified and decarboxylated by heating.

Compounds of formula I, in which X is $CONHR^1$ may be prepared by treatment of a corresponding compound of formula I wherein X is COCl or $CO_2R^1$ and $R^1$ is alkyl with ammonia to give a compound of formula I in which X is $CONH_2$, which may be subsequently alkylated to introduce the group $R^1$ when alkyl. Conveniently a compound of formula I wherein X is $CO_2R^1$ wherein $R^1$ is lower alkyl, especially methyl or ethyl, is treated with ammonia. Alternatively substituted amides of formula I wherein X is $CONHR^1$ wherein $R^1$ is alkyl may be prepared by treatment of the carboxylic ester of formula I wherein X is $CO_2R^1$ and $R^1$ is alkyl with an amine of formula $R^1NH_2$ wherein $R^1$ is alkyl. The substituted amides may also be prepared from the acid chloride of formula I wherein X is COCl by treatment with a primary amine $R^1NH_2$ wherein $R^1$ is alkyl.

Examples of primary amines which may be used in the above reactions are methylamine and n-butylamine.

The acid chlorides may be prepared by treatment of the corresponding acid of formula I, wherein X is $CO_2H$ with thionyl chloride, phosphorus oxychloride or phosphorus pentachloride.

A further process for preparing compounds of formula I as defined above wherein X is $CONHR^1$ and $R^1$ is hydrogen or alkyl, comprises treating an ester compound of formula I, wherein X is $CO_2R^1$ and $R^1$ is alkyl with an amide of formula $R^6CONHR^1$ or a salt thereof wherein $R^1$ is hydrogen or alkyl and $R^6$ is hydrogen or lower alkyl in the presence of an alkali-metal alkoxide or sodamide.

Preferably a molar equivalent of alkali-metal alkoxide is used for each mole of ester of formula I. The alkali-metal alkoxide may be one derived from a lower alkanol having from 1 to 6 carbon atoms e.g. methanol or ethanol. The alkali-metal is preferably sodium.

The ester of formula I is preferably a lower alkyl ester.

The amide $R^6CONHR^1$ is preferably one in which $R^6$ is hydrogen or methyl. $R^1$ is also preferably hydrogen or methyl. Thus preferred amides are formamide, N-methylformamide, acetamide and N-methylacetamide. Salts, especially alkali-metal salts of these amides may be used as starting materials.

The reaction may be carried out by heating the reactants together.

The amides of formula I, wherein X is $CONH_2$ may also be prepared by partial hydrolysis of the corresponding nitriles of formula I, wherein X is CN. This hydrolysis may be accomplished in conventional manner e.g. by concentrated (e.g. 96%) sulphuric acid.

Thioamides of formula I wherein X is CSNH $R^1$ wherein $R^1$ is hydrogen or alkyl may be prepared by treatment of the corresponding compounds in which X is $CONHR^1$ with $P_2S_5$ e.g. by refluxing in pyridine. As mentioned below when the starting material is one in which X is $CONH_2$ decomposition to the nitrile may occur. This decomposition can be avoided by conducting the $P_2S_5$ reaction in the presence of $H_2S$. Alternatively the thioamides may be prepared by treatment of a nitrile of formula I, wherein X is CN with $H_2S$ to give the unsubstituted thioamide wherein X is $CSNH_2$. Substituted thioamides may be obtained by conducting this reaction in the presence of a primary amine $R^1NH_2$ wherein $R^1$ is alkyl. The $H_2S$ reaction can be carried out in a suitable solvent in the presence of a catalyst such as a tertiary amine e.g. a trialkylamine such as triethylamine, or diiospropylamine in ethanol.

The nitrile of formula I wherein X is CN, may be prepared by dehydration of the corresponding amides of formula I wherein X is $CONH_2$. Such dehydration can be carried out with $P_2O_5$ as the dehydrating agent. Other dehydrating agents are phosphorus pentachloride or thionyl chloride. Dehydration of an amide to a nitrile may also be effected by heating the amide in hexamethylphosphorictriamide as solvent. When using this solvent a compound of formula I in which X is $CONMe_2$ may be formed as a significant by-product.

The nitriles may also be formed when the amide is treated with $P_2S_5$. It is believed that the thioamide is first formed and decomposes to the nitrile. The nitrile can either be separated, e.g. by chromatography or the mixture treated with $H_2S$ for conversion of the nitrile to the corresponding thioamide.

A further process for preparing compounds of formula I wherein X is $CSNHR^1$ and $R^1$ is alkyl comprises reacting a compound of formula (IV) with a compound of formula $R^1NCS$ wherein $R^1$ is alkyl and then treating the product with hydrogen ions.

Preferably a starting material of formula IV wherein M is lithium or MgHal is used. Conveniently, the product after reaction with $R^1NCS$ is treated with acid e.g. an aqueous mineral acid such as a hydrohalic acid, preferably hydrochloric acid. A preferred compound $R^1NCS$ is methyl isothiocyanate.

A further method for preparing the thioamides of formula I, wherein X is $CSNH_2$ comprises reacting a nitrile of formula I wherein X is CN with a thioamide of formula $R^7CSNH_2$ where $R^7$ is an alkyl group, e.g. a lower-alkyl group of 1–6 carbon atoms, preferably a methyl group, in a suitable solvent such as dimethyl formamide saturated with hydrogen chloride.

The starting materials of formula I wherein X is hydrogen are either known compounds or may be prepared by processes for preparing analogous compounds e.g. by the following reaction scheme.

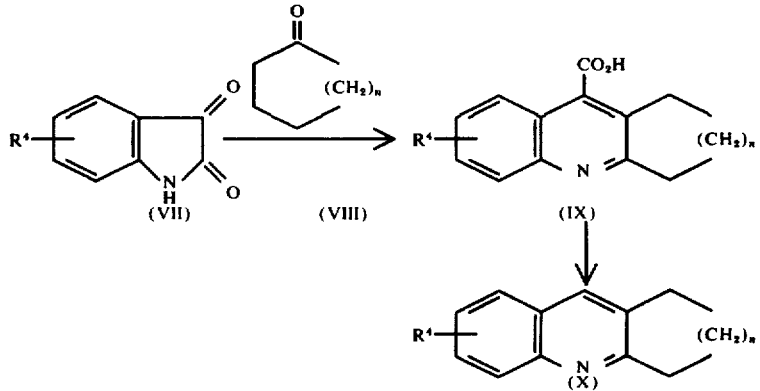

In the above scheme the isatin VII wherein $R^4$ is as defined in connection with formula I is reacted with ketone VIII wherein n is 1, 2 or 3 under basic conditions to give compound (IX). The group $R^3$ may be introduced by modification of the carboxyl group in compound (IX) in known manner. The group $R^2$ may be introduced by starting with an appropriately substituted ketone (VIII).

The invention also includes pharmaceutical compositions comprising a compound of formula I wherein X is $CSNHR^1$ and a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 5mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients, e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

The invention is illustrated by the following examples:

EXAMPLE 1

1,2,3,4-Tetrahydroacridine-4-thiocarboxamide

A solution of isatin (40 g. 0.272 mol) in 30% aqueous potassium hydroxide (160 ml., 1.5 mol.) was added to a solution of cyclohexanone (69.7 g. 0.712 mol.) in ethanol (300 ml.) and the mixture heated at reflux with stirring for 10 hours. The ethanol was removed in vacuo and the residue dissolved in water (400 ml.) and extracted with ether (3 × 50 ml.). The aqueous phase was acidified with acetic acid and the resultant solid was washed with water, dried and heated at 310° C in a Wood's metal bath for 35 minutes. The cooled melt was diluted with 2N HCl (200 ml.) and extracted with chloroform (2 × 200 ml.) and the extracts discarded. The aqueous phase was adjusted to pH 9.0 with sodium carbonate and extracted with ethyl acetate (4 × 100 ml.) The combined extracts were washed with brine, dried and the solvent removed and the residual oily solid recrystallised from (bp 40°–60°) petrolum ether to give 1,2,3,4-tetrahydroacridine as colourless needles (38 g.). A sample (1 g.) was dissolved in anhydrous ether and treated with ethereal hydrogen chloride. The resultant solid was removed and recrystallised from isopropanol to give 1,2,3,4-tetrahydroacridine hydrochloride quarter hydrate as colourless needles m.p. 232° C. (Found C,70.2; H,6.5; N,5.9, $C_{13}H_{13}N.HCl.$ ¼$H_2O$ requires: C,69.7; H, 6.5; N, 6.2%).

A solution of 1,2,3,4-tetrahydroacridine (3.66 g., 0.02 mol.) in anhydrous benzene (5 ml.) was cooled to 0° C and treated dropwise with a 10% (w/v) solution of butyl lithium in hexane (14 ml., 0.022 mol.) and allowed to stand at 0° C for 1 hour. The solution was treated dropwise with a solution of trimethylsilylisothiocyanate (3.2 ml., 0.02 mol.) in benzene (2 ml.) and allowed to stand at 0° C for 30 minutes. The reaction mixture was treated with water (10 ml.) and then with 2NHCl (10 ml) and the resultant solid removed by filtration, washed with water (2 × 5 ml.) and ethyl acetate (3 × 10 ml.) and the combined filtrates retained for recovery of 1,2,3,4-tetrahydroacridine (1.3 g.). The solid was recrystallised from water to give the hemihydrate of the hydrochloride of the title compound as a pale yellow powder (3.5 g., 61%) m.p. 239° C (dec.) (Found: C, 58.5; H, 5.9; N, 9.5, $C_{14}H_{14}N_2S.HCl.$ ½ $H_2O$ requires: C,58.4; H,5.6; N, 9.9%).

1,2,3,4-Tetrahydroacridine-4-thiocarboxamide displayed anti-ulcer activity in the test of Brodie & Hanson; J. Applied Physiology 15, 291, 1960.

EXAMPLE 2

1,2,3,4-Tetrahydroacridine-4-(N-methyl)-thiocarboxamide

A solution of 1,2,3,4-tetrahydroacridine (2.15g, 0.012 mole) in benzene (10 ml) was cooled in ice and treated dropwise with n-butyl lithium solution (9% w/v, 9.2 ml, 0.012 mole) with stirring. After 1 hour a solution of methylisothiocyanate (0.934 g, 0.012 mole) in benzene (15 ml) was added and the mixture was stirred for 1 hour. The resulting solution was treated with water (5 ml) and acidified with 2N HCl. The aqueous layer was separated and the organic layer was extracted with 2N HCl. The combined acid extracts were washed with ethyl acetate, basified with solid sodium carbonate and extracted with chloroform. The chloroform solution was dried over $MgSO_4$, filtered and evaporated to give 1,2,3,4-tetrahydroacridine-4(N methyl)-thiocarboxamide (2.26 g, 70%). It was dissolved in hot isopropyl alcohol, excess ethereal HCl was added and the hydrochloride allowed to crystallise as needles m.p. 265° C decomp (Found: C,61.8; H, 6.1; N, 9.5. $C_{15}H_{16}N_2S.$ HCl requires C, 61.5; H, 5.8; N, 9.6%).

1,2,3,4-Tetrahydroacridine-4(N-methyl)thiocarboxamide and its acid addition salts are anti-ulcer agents which display good anti-secretory in the tes of H. Shay, D. Sun and H. Greenstein Gastroenterology 1954, 26, 906–13.

EXAMPLE 3

Using the method of Example 1 the following starting materials may be reacted with butyl-lithium and the product treated in situ with trimethylsilyl isothiocyanate to give the following products.

| Starting Material | Product |
| --- | --- |
| 1,2,3,4-Tetrahydro-2-methylacridine | 1,2,3,4-Tetrahydro-2-methylacridine-4-thiocarboxamide |
| 1,2,3,4-Tetrahydro-3-methylacridine | 1,2,3,4-Tetrahydro-3-methylacridine-4-thiocarboxamide |
| 1,2,3,4-Tetrahydro-6-methylacridine | 1,2,3,4-Tetrahydro-6-methylacridine-4-thiocarboxamide |
| 1,2,3,4-Tetrahydro-7-methylacridine | 1,2,3,4-Tetrahydro-7-methylacridine-4-thiocarboxamide |
| 1,2,3,4-Tetrahydro-9-methylacridine | 1,2,3,4-Tetrahydro-9-methylacridine-4-thiocarboxamide |

EXAMPLE 4

Using the method of Example 2 the following starting materials may be reacted with butyl lithium and the product treated in situ with methylisothiocyanate to give the following products.

| Starting Material | Product |
| --- | --- |
| 1,2,3,4-Tetrahydro-2-methylacridine | 1,2,3,4-tetrahydro-2-methylacridine-4-(N-methyl)-thiocarboxamide |
| 1,2,3,4-Tetrahydro-3-methylacridine | 1,2,3,4-tetrahydro-3-methylacridine-4-(N-methyl)-thiocarboxamide |
| 1,2,3,4-Tetrahydro-6-methylacridine | 1,2,3,4-tetrahydro-6-methylacridine-4-(N-methyl)-thiocarboxamide |
| 1,2,3,4-Tetrahydro-7-methylacridine | 1,2,3,4-tetrahydro-7-methylacridine-4-(N-methyl)-thiocarboxamide |
| 1,2,3,4-Tetrahydro-9-methylacridine | 1,2,3,4-tetrahydro-9-methylacridine-4-methyl)-thiocarboxamide |

EXAMPLE 5

Examples 2 and 4 may be repeated substituting ethylisothiocyanate and then n-butylisothiocyanate for methylisothiocyanate to obtain the corresponding N-ethyl and N-butyl thiocarboxamides.

EXAMPLE 6

2,3-Dihydro-1H-cyclopenta[b]quinoline-3-thiocarboxamide 2,3-Dihydro-1H-cyclopenta[b] quinoline in ether is added to isopropylmagnesium bromide (prepared from magnesium and isopropylbromide in ether). The mixture is heated at 120° C for several hours adding toluene when necessary as the ether distilled off to maintain the contents liquid. The mixture is cooled and ether is added. The resulting solution of 2,3-dihydro-1H-cyclopenta[b]-quinoline-3-magnesium bromide is added to stirred ice-cooled ether while a stream of dry $CO_2$ gas is bubbled through until the red colour is discharged. The resulting solid (the magnesium bromide salt of 2,3-dihydro-1H-cyclopenta[b] quinoline-3-carboxylic acid) is dried and added to methanol saturated with HCl. The solution is stirred overnight and then evaporated to dryness. The residue is dissolved in water and extracted with ether. The aqueous phase is basified with sodium carbonate, any solid filtered off and the aqueous solution is extracted with ether (3 times). The ether extracts are dried and evaporated to dryness leaving an oil which is purified by distillation under reduced pressure to give methyl 2,3-dihydro-1H-cyclopenta[b] quinoline-3-carboxylate. This ester is dissolved in methanol saturated with ammonia in a bomb and kept overnight at 80° C. The solution is then cooled and evaporated to dryness. Purification and recrystallisation of the product gives 2,3-dihydro-1H-cyclopenta [b] quinoline-3-carboxamide.

The amide is dissolved in pyridine and a slight molar excess of $P_2S_5$ is added. The mixture is stirred under reflux while bubbling $H_2S$ through the solution for several hours. The mixture is then cooled and evaporated to dryness. The residue is treated with 10% NaOH to produce a strongly basic emulsion which is extracted with ether (3 times). The etheral extracts are washed with water and extracted with 2N HCl (3 times). The acid extract is basified to pH 10 with sodium carbonate and extracted with ether. The ethereal extracts are washed with water and dried over $MgSO_4$, filtered and evaporated to dryness. The resulting product 2,3-dihydro-1H-cyclopenta[b]quinoline-3-thiocarboxamide is recrystallised and may be converted to its hydrochloride by treatment with ethereal HCl.

I claim:

1. A compound of the formula:

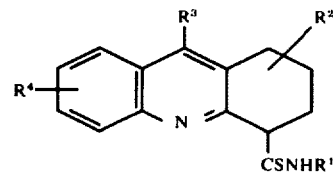

or a pharmaceutically acceptable acid addition salt thereof,
wherein
$R^1$, $R^2$, $R^3$ and $R^4$ are independently selected from the group consisting of hydrogen and alkyl of 1 to 6 carbon atoms.

2. A compound of claim 1 of the formula:

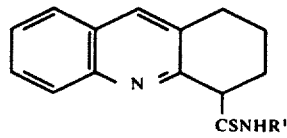

or a pharmaceutically acceptable acid addition salt thereof, wherein $R^1$ is hydrogen or alkyl of 1 to 6 carbon atoms.

3. A compound of claim 1 of the formula:

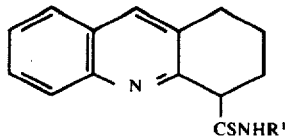

or a pharmaceutically acceptable acid addition salt thereof, wherein R¹ is hydrogen or methyl.

4. A compound of claim 1 wherein is 1,2,3,4-tetrahydroacridine-4-thiocarboxamide or a pharmaceutically acceptable acid addition salt thereof.

5. A compound of claim 1 which is 1,2,3,4-tetrahydroacridine-4(N-methyl)thiocarboxamide or a pharmaceutically acceptable acid addition salt thereof.

6. A pharmaceutical composition comprising an effective amount of an anti-ulcer agent of the formula:

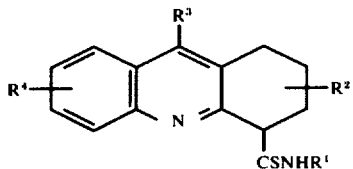

or a pharmaceutically acceptable acid addition salt thereof, wherein $R^1$, $R^2$, $R^3$ and $R^4$ are independently hydrogen or alkyl of 1 to 6 carbon atoms; and a pharmaceutically acceptable carrier.

7. A pharmaceutical composition of claim 6 in which said anti-ulcer agent is 1,2,3,4-tetrahydroacridine-4-thiocarboxamide or a pharmaceutically acceptable acid addition salt thereof.

8. A pharmaceutical composition of claim 6 in which said anti-ulcer agent is 1,2,3,4-tetrahydroacridine-4(N-methyl)-thiocarboxamide or a pharmaceutically acceptable acid addition salt thereof.

* * * * *